United States Patent [19]

Sugiyama et al.

[11] Patent Number: 4,859,767

[45] Date of Patent: Aug. 22, 1989

[54] GLUCOSYLMORANOLINE DERIVATIVES AND USE THEREOF FOR INHIBITING INCREASE IN BLOOD SUGAR LEVELS

[75] Inventors: Makoto Sugiyama, Kyoto; Yoji Ezure, Otsu; Yoshiaki Yoshikuni, Uji; Takayuki Ozaki; Nobutoshi Ojima, both of Moriyama, all of Japan

[73] Assignee: Nippon Shinyaku Co., Ltd., Japan

[21] Appl. No.: 917,739

[22] Filed: Oct. 10, 1986

[30] Foreign Application Priority Data

Oct. 12, 1985 [JP] Japan .................................. 60-227601
May 14, 1986 [JP] Japan .................................. 61-111618

[51] Int. Cl.$^4$ ..................... C07H 15/00; C07H 17/00; A61K 31/70
[52] U.S. Cl. .................................. 536/17.4; 536/17.9; 514/866
[58] Field of Search ................. 536/17.4, 17.9; 514/23, 514/866, 25

[56] References Cited

U.S. PATENT DOCUMENTS 4,338,433  7/1982  Matsumura et al. ................. 514/866
4,363,802  12/1982  Matsumura et al. ................. 536/17.4

FOREIGN PATENT DOCUMENTS 0186103  7/1986  European Pat. Off. ............ 514/866
2067989  8/1981  United Kingdom ................ 514/866
2067990  8/1981  United Kingdom ................ 514/866

OTHER PUBLICATIONS

Robbins; *The Pathologic Basis of Disease;* pp. 272–273.

Primary Examiner—Ronald W. Griffin
Assistant Examiner—Nancy S. Carson
Attorney, Agent, or Firm—Jacobs & Jacobs

[57] ABSTRACT

Compounds of formula I are useful in the prophylaxis or treatment of hyperglycemic symptoms

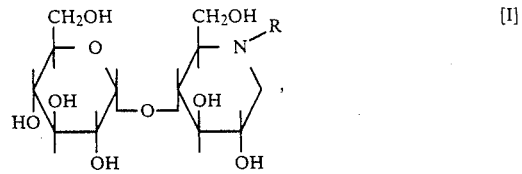

wherein R is alkyl substituted by one or more hydroxy.

15 Claims, No Drawings

GLUCOSYLMORANOLINE DERIVATIVES AND USE THEREOF FOR INHIBITING INCREASE IN BLOOD SUGAR LEVELS

The present invention is directed to compounds of formula (I)

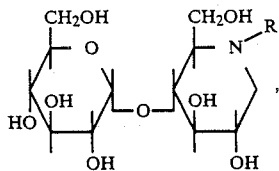

in which R is alkyl substituted by one or more hydroxyl moieties. Compounds (I) are useful as agents that inhibit blood sugar level increase.

Moranoline, which is represented by the formula (II) below, has been isolated from Mori Cortex, which is a crude drug of natural origin (cf. Yagi, et al., Nippon Nogei Kagaku Kaishi, volume 50, page 571, 1976 and Japanese published patent application No. 52-83951):

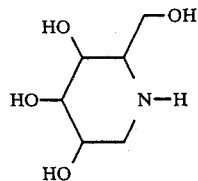

Moranoline (II) has also been manufactured by fermentation using microorganisms belonging to the genus Streptomyces (cf. Japanese published patent application No. 54-84094).

While moranoline (II) exhibits inhibitory action against blood sugar increase in animals loaded with sugar, and it is useful in the treatment of diabetes mellitus, derivatives having an improved effect have been proposed, namely 4-(alpha-D-glucosyl)-moranoline and 4-(alpha-D-glucosyl)-N-lower alkylmoranolines represented by the following structural formula (III), (cf. Japanese published patent application Nos. 54-159417 and 55-76838):

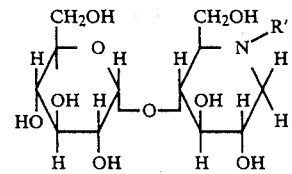

(where $R^1$ represents H or lower alkyl)

The compounds (I) of the invention have a stronger inhibitory action against blood sugar increase with less toxicity than moranoline (II) and the moraniline derivitives (III) and hence are useful in the treatment of diabetes mellitus.

The characteristic feature of the compounds (I) of the present invention is the hydroxy-substituted alkyl group located at the nitrogen atom in the ring. There does not appear to be any limitation on the number of hydroxy substituents, and generally from about 1 to about 8, preferably from about 1 to about 4, hydroxy groups will be present. Similarly, there does not appear to be any limitation on the number of carbon atoms in the alkyl moiety, and generally from about 1 to 8, preferably from about 1 to about 4, carbon atoms will be present. The term "alkyl" as used herein includes both straight and branched chain alkyl.

Representative compounds (I) of the present invention include:
4-O-alpha-D-Glucopyranosyl-N-(2-hydroxyethyl)-moranoline;
4-O-alpha-D-Glucopyranosyl-N-(2-hydroxypropyl)-moranoline;
4-O-alpha-D-Glucopyransoyl-N-(3-hydroxypropyl)-moranoline; and
4-O-alpha-D-Glucopyranosyl-N-(2,3-dihydroxypropyl)moranoline.

Compounds (I) are basic and, accordingly, form salts with various types of acids. The present invention includes compounds (I) and pharmaceutically acceptable salts thereof.

Compounds (I) may be prepared by treating 4-O-alpha-D-glucopyranosylmoranoline, i.e. compound III in which R' is hydrogen, with an epoxide in an inert solvent; or with a beta-halohydrin in a polar solvent; or with an alpha-haloketone followed by reduction to provide the hydroxy group or groups.

Alternatively, compounds (I) can be prepared by reacting N-hydroxyalkyl moranoline (IV)

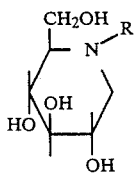

in solution with cyclodextrin or soluble starch, followed by reaction with cyclodextringlycosyltransferase to give the oligoglucosylmoranoline derivative (V)

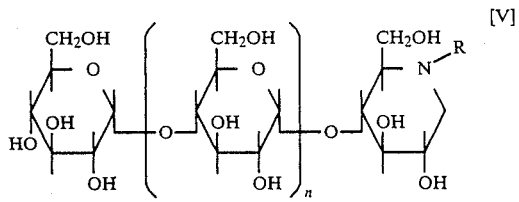

wherein R is as defined above and n is an integer from zero to about 15. Compound (V) may be isolated from the reaction mixture by any suitable means, such as column chromatography. If desired, the reaction solution containing compound (V) may be used as such in the next reaction step, wherein compound (V) is reacted with a glucoamylase to provide compound (I). Glucoamylase available in the market may be used. After the reaction, compound (I) may be isolated by, for example, a column chromatography. Compound (I) may be purified by a conventional column chromatographic technique such as with Sephadex G-15.

The inhibitory action of compounds (I) of the present invention against blood sugar level increase was confirmed by the following tests.

Starch (soluble starch; Kanto Kagaku KK) (2 g/kg) was given orally to four male beagles (26 months of age; 11–14 kg body weight) and the inhibitory effect of the present invention compound given orally at the same time against blood sugar level increase was tested. Starch (20 g) was added to 100 ml of water followed by heating to dissolve the starch and 10 ml of the solution per 1 kg of body weight was administered. Blood was taken from the artery of front and central part of the forepaw at predetermined time intervals and 25 microliters of blood was placed in an YS-1 glucoanalyzer (model 23A) (manufactured by K. K. Nikkaki) to determine the blood sugar level. The group administered with starch only and that with water (10 ml/kg body weight) only were named control and basal, respectively, and the test compound was administered orally to the animals in doses of 1, 3, and 10 mg/kg together with starch. During the test, four beagles were kept at a constant temperature (23°±2° C.) and a constant humidity (55±5%) with a dark-bright cycle every 12 hours and, in the evening, 300 g of dog food (CD-1, manufactured by Nippon Kurea K.K.) was given daily. The results of four examples of each test group is given in Table 1. The values therein is (average value)±(-standard deviation).

It is apparent from the result that the compounds (I) of the present invention exhibit an inhibitory action against blood sugar level increase.

TABLE 1

| Compound + Dose (Example Number) | Blood Sugar Level (mg/dl) | | | |
|---|---|---|---|---|
| (mg/kg) | 0 min | 15 min | 30 min | 45 min |
| 1 Basal | 56 ± 2 | 57 ± 3 | 55 ± 2 | 56 ± 2 |
| 2 Control | 56 ± 2 | 87 ± 12 | 113 ± 13 | 116 ± 6 |
| 3 1 (1) | 56 ± 1 | 77 ± 8 | 94 ± 3 | 94 ± 6 |
| 4 1 (3) | 54 ± 2 | 69 ± 5 | 77 ± 8 | 86 ± 6* |
| 5 1 (10) | 56 ± 2 | 68 ± 3 | 73 ± 5* | 69 ± 2* |
| 6 2 (1) | 57 ± 2 | 63 ± 2 | 106 ± 5 | 118 ± 6 |
| 7 2 (3) | 56 ± 1 | 84 ± 12 | 104 ± 4 | 100 ± 6 |
| 8 2 (10) | 55 ± 2 | 60 ± 2 | 71 ± 6* | 81 ± 7* |

| | Blood Sugar Level (mg/dl) | | | |
|---|---|---|---|---|
| | 60 min | 75 min | 90 min | 120 min | 180 min |
| 1 | 56 ± 1 | 54 ± 1 | 55 ± 2 | 52 ± 2 | 50 ± 1 |
| 2 | 114 ± 6 | 90 ± 8 | 68 ± 6 | 53 ± 3 | 52 ± 2 |
| 3 | 86 ± 6* | 87 ± 6 | 80 ± 4 | 66 ± 1 | 53 ± 3 |
| 4 | 82 ± 4** | 81 ± 4 | 77 ± 2 | 65 ± 4 | 53 ± 2 |
| 5 | 68 ± 3*** | 72 ± 3 | 65 ± 1 | 65 ± 4 | 50 ± 3 |
| 6 | 113 ± 11 | 98 ± 9 | 82 ± 4 | 60 ± 3 | 51 ± 2 |
| 7 | 92 ± 5* | 78 ± 3 | 69 ± 2 | 65 ± 1 | 52 ± 2 |
| 8 | 87 ± 5* | 78 ± 5 | 74 ± 1 | 64 ± 3 | 52 ± 1 |

* $P < 0.05$,  $P < 0.01$, * $P < 0.001$

When the present invention compounds (Examples 1 and 2) were orally given to mice at 5 g/kg for checking the toxicity, there was no case of death. When the present invention compounds (Examples 1 and 2) were administered at 400 mg/kg to rats for consecutive five days by intraperitoneal route, there was no abnormal observation in clinical state, biochemical values of serum, and hematological data at all. Thus, the toxicity of the present invention compounds is very little.

The present invention provides a pharmaceutical composition for prophylaxis or treatment of hyperglycemic symptoms, which comprises an amount of compound (I) effective to inhibit the increase of blood sugar, together with a pharmaceutically acceptable non-toxic, inert diluent or carrier therefor.

The present invention also provides a method for the prophylaxis or treatment of hyperglycemic symptoms in humans and animals, which comprises administering to a human or animal in need thereof an amount of compound I effective to inhibit the increase of blood sugar.

Compounds (I) are used in the same manner as known inhibitors of blood sugar level increase, such as the known moranoline derivatives.

Compounds (I) can be administered as such or in the form of the above pharmaceutical composition containing, for example, 0.1 to 99.5% or preferably 0.5 to 90% of compound (I) and a pharmaceutically acceptable non-toxic inert carrier. The carrier may be one or more solid, semisolid or liquid diluent, filler or auxiliary agent used for pharmaceutical preparations. The pharmaceutical composition is preferably administered in a form of unit dose.

Compounds (I) may be administered orally, parenterally, topically or by rectum. Oral administration is especially preferred.

Suitable dosages for diabetes mellitus will be determined by taking into account the state of the patient (e.g. age, body weight, etc.), administration route, type and degree of the disease, and the like. Usually it is preferred that the daily dose range from about 10 to 2000 mg and, more preferably from about 100 to about 600 mg. In some cases, a smaller dose may be sufficient while, in other cases, a larger dose may be necessary. It may also preferred that the daily dose is divided when given to the patient.

The present invention is further illustrated by the following Examples.

EXAMPLE 1A

4-O-alpha-D-Glucopyranosylmoranoline (10 g) was dissolved in 150 ml of hot dimethyl sulfoxide and 16 g of potassium carbonate was added thereto. Ethylene bromohydrin (18 g) was added thereto with stirring and the mixture was made to react at 100°–110° C. for 3 hours. After the reaction, the mixture was filtered to remove the insoluble matter, then 150 ml of water was added, and the mixture was gently stirred. This was passed through 300 ml of strongly acidic ion exchange resin (Dowex 50W×2 (H+)) so that the object compound was adsorbed therein. The column was well washed with water, eluted with 0.5N ammonia water, the eluate was concentrated in vacuo, then treated with an activated carbon, and concentrated to dryness in vacuo. To this was added acetone and the matter which was soluble in acetone was removed. The acetone-insoluble matter was dissolved in suitable amount of hot water and was crystallized using ethanol. Crystals were collected by filtration and were similarly recrystallized and 6.0 g of the final product, i.e. 4-O-alpha-D-glucopyranosyl-N-(2-hydroxyethyl)moranoline was obtained.

M.p. 98°–101° C.

$[\alpha]_D^{24} = +76.7°$ (1%, water)

Example 1B.

Manufacture of the same compound as in Example 1A utilizing enzymes, is disclosed in this example.

Culture of Bacillus mascerans

A culture liquid (100 ml; pH 7) containing 1% corn steep liquor, 1% soluble starch, 0.5% ammonium sulfate and 0.5% calcium carboante was placed in a 500 ml Erlenmeyer flask and sterilized by heating at 120° C. for 15 minutes. Three platinum loops of Bacillus macerans IFO 3490 strain fully grown on a slant medium of 1% peptone, 0.5% yeast, 0.3% glucose, 1.5% glycerol, 0.3% sodium chloride, 2.5% liver powder (OXOID-trademark), and 1.5% agar were inoculated thereupon and subjected to a shake culture at 37° C. for 3 days.

The culture liquid (600 ml) was inoculated on 18 liters of the medium of the same composition in a 30 liter jar fermentor and cultured at 37° C. for 3 days with full aeration and stirring to give an enzyme solution of 130 to 150 units as a supernatant liquid after centrifugation.

Unit of activity of cyclodextrin glycosyltransferase

In 0.05M acetate buffer (pH 5.5) was dissolved 0.7% of soluble starch (for biochemical study; manufactured by Nakarai Chemical Co) to prepare a substrate solution. To 950 microliters of this substrate solution was added 50 microliters of enzyme solution, the mixture was made to react at 40° C. for 10 minutes, and the reaction was made stopped by addition of 0.5 ml of 0.5N acetic acid. After the reaction, 100 microliters of the reaction solution was taken out and 3 ml of water and 0.8 ml of iodine solution (in 0.25M potassium iodide solution was added iodine to make its concentration 0.01M) were added thereto. The mixture was stirred and the extinction at 660 nm was measured (an AT value). Similarly, to 950 microliters of the substrate solution were added 50 microliters of water and 0.5 ml of 0.5N acetic acid and 100 microliters of the resulting mixture was treated with the iodide solution and the extinction at 660 nm was measured (an AR value).

$$One\ unit = [(AR - AT)/AR] \times 100 \times 2$$

This one unit is an activity causing a decrease of 1% extinction of the enzyme solution at 40° C. for 1 minute.

Preparation of the crude enzyme solution

The culture liquid of B. macerans IFO 3490 is centrifuged to give a supernatant liquid. This was lyophilized, dissolved in small quantities of water, and a concentrated enzyme solution was obtained. This was well dialyzed at 5° C. to water and the inner solution free from low molecular substances was used as an enzyme solution. If necessary, it was lyophilized and the resulting powder was used.

N-(2-Hydroxyethyl)moranoline (5 g) was dissolved in small amount of water, the solution was adjusted to pH 5.7 with 3N hydrochloric acid, and made 25 ml with water. alpha-Cyclodextrin (80 g) was dissolved in 3975 ml of crude enzyme solution (250 units/ml), N-(2-hydroxyethyl)moranoline solution was added thereto, and the mixture was readjusted to pH 5.7. This was shaken at 40° C. for 3 days to cause a reaction. The reaction solution was centrifuged, the supernatant liquid was passed through a column (200 ml) of Dowex 5oW×2 (H+), strongly acidic ion exchange resin, so that basic substances were adsorbed. The column was well washed with water, eluted with 0.5N ammonia water, the eluate was concentrated to dryness in vacuo, and 14.8 g of mixture of oligoglucosyl-N-(2-hydroxyethyl)moranolines was obtained.

This was analyzed by a high-speed liquid chromatography and was found to be a mixture of 15% of N-(2-hydroxyethyl)moranoline and 85% of oligoglucosyl-N-(2-hydroxyethyl)moranoline. The conditions for said high-speed liquid chromatography were as follows.

Sumipax R741 (Nucleosil 5NH2, 5 micrometers, 4 mm ID×25 cm). Solvent: acetonitrile-water (65/35). Rate of liquid flow: 1 ml/min. RI Detection (Elmer Optical Co., ERC-7510). Data processor (manufd by Hitachi Ltd., 655-60).

The oligoglucosyl-N-(2-hydroxyethyl)moranoline mixture (10 g) obtained hereinabove was dissolved in 50 ml of water and the solution was adjusted to pH 5.1. Water was added thereto to make the total volume 100 ml and 250 ml of glucoamylase (Glucozyme AF-6, manufd by Nagase Sangyo Co) was added. The mixture was made to react at 50° C. for 24 hours, the reaction was ceased by heating at 80° C., and cooled to ambient temperature. The reaction solution was centrifuged, the supernatant liquid was passed through a column (200 ml resin volume) of strongly acidic ion exchange resin, and the column was well washed with water. The column was then eluted with 0.5N ammonia water and the eluate was concentrated to dryness in vacuo to give 5.6 g of powder.

This was subjected to an analysis by a high-speed chromatography the same as before and found to be a mixture of 28.8% of N-(2-hydroxyethyl)moranoline, 71.0% of 4-O-alpha-D-glucopyranosyl-N-(2-hydroxyethyl)moranoline, and 0.2% of 4-O-alpha-D-maltosyl-N-(2-hydroxyethyl)moranoline.

EXAMPLE 1C

Soluble starch (8 g) was dissolved in 50 ml of hot water 1 g of N-(2-hydroxyethyl)moranoline was dissolved therein. The solution was cooled to 40° C., adjusted to pH 5.7, and 50 ml of a crude enzyme solution (4000 units/ml) was added thereto. This was readjusted to 5.7 and made to react at 40° for 3 days with shaking. The reaction was ceased by heating at 80° C. for 20 minutes, cooled to 50° C., adjusted to pH 5.1, 500 ml of glucoamylase (Glucozyme AF-6, manufd by Nagase Industry Co) was added thereto, and the mixture was made to react at 50° C. for 24 hours. The reaction was ceased by heating at 80° C. for 20 minutes, cooled to ambient temperature, and centrifuged. The supernatant liquid was passed through a column (100 ml of resin) of strongly acidic ion exchange resin Dowex 50W×2 (H+) to make basic substances adsorbed. The column was well washed with water, eluted with 0.5N ammonia water, and the eluate was concentrated to dryness in vacuo to give 1.8 g of powder.

This was analyzed by a high-speed liquid chromatography and found to be a mixture of 29% of N-(2-hydroxyethyl)moranoline, 70% of 4-O-alpha-D-glucopyranosyl-N-(2-hydroxyethyl)moranoline, and 1% of 4-O-alpha-D-maltosyl-N-(2-hydroxyethyl)moranoline. The high-speed liquid chromatographic condition was the same as above with an exception that the developer was a mixture of acetonitrile and water (70:30).

The above mixture powder (1.5 g) was dissolved in small amount of water, the solution was passed through a column (48 mm diameter × 850 mm) of Sephadex G-15 and the column was developed with distilled water wherefrom each 5 ml of fraction was collected.

Each fraction was analyzed by a high-speed liquid chromatography to collect desired fractions were combined and concentrated to dryness in vacuo. The resulting powder was recrystallized from aqueous ethanol to give 550 mg. of 4-O-alpha-D-glucopyranosyl-N-(2-hydroxyethyl)moranoline. M.p. 99°–102° C. $[\alpha]_D^{25} = +76.5°$ (1%, water).

Example 2A

4-O-alpha-D-Glucopyranosylmoranoline (10 g) was dissolved in 150 ml of hot dimethyl sulfoxide and 16 g of potassium carbonate was added thereto. Epibromohydrin (20 g) was added thereto with stirring and the mixture was made to react at 100°–110° C. for 3 hours.

After the reaction, the mixture was filtered to remove the insoluble matter. Water (150 ml) was added thereto and the mixture was gently stirred. This was passed through a column of 300 ml of strongly acidic ion exchange resin (Dowex 50W×2 (H+)) and the object compound was adsorbed therein. The column was well washed with water, eluted with 0.5N ammonia water, the eluate was refluxed with stirring at 80° C. for 3 hours, concentrated in vacuo, treated with an activated carbon, passed through a column of 200 ml of Diaion HP-200, and washed with water. The passed solution and washing solution were combined, the mixture was concentrated in vacuo, the concentrate was dissolved in methanol, the methanolic solution was treated with 3 liters of Sephadex LH-20, the column was developed with methanol, fractions containing the object compound were collected, then methanol was evaporated therefrom, the residue was dissolved in suitable quantity of hot water, and crystallized with ethanol. Crystals were collected by filtration and similarly recrystallized to give 5.0 g of the final product, i.e. 4-O-alpha-D-glucopyranosyl-N-(2,3-dihydroxypropyl)moranoline. m.p. 83°–85° C. $[\alpha]_D^{24} = +73.7°$ (1%, water)

EXAMPLE 2B

Manufacture of the same compound as in Example 2A utilizing enzymes, is disclosed in this example.

Soluble starch (8 g) was dissolved in 50 ml of hot water and 1 g of N-(2,3-dihydroxypropyl)moranoline was dissolved therein. The solution was cooled to 40° C., adjusted to pH 5.7, and 50 ml of crude enzyme solution (4000 units/ml) was added thereto. The solution was readjusted to pH 5.7 and made to react at 40° C. for 3 days with shaking. Then this was treated by similar manner as Example 2 to give 1.6 g of mixture of 31% of N-(2,3-hydroxypropyl)moranoline, 68% of 4-O-alpha-D-glucopyranosyl-N-(2,3-dihydroxypropyl)moranoline, and 1% of 4-O-alpha-D-maltosyl-N-(2,3-dihydroxypropyl)moranoline.

This mixture powder (1.5 g) was dissolved in small amount of waer, the solution was passed through a column (48 mm diameter×850 mm) of Sephadex G-15, developed with distilled water, and each 5 ml of fraction was collected. Each fraction was analyzed by a high-speed liquid chromatography to collect object fractions and concentrated to dryness in vacuo. The resulting powder was recrystallized from aqueous ethanol to give 505 mg of 4-O-alpha-D-glucopyranosyl-N-(2,3-dihydroxypropyl)moranoline. M.p. 83°–86° C. $[\alpha]_D^{25} = +72.3°$ (1%, water).

EXAMPLE 3

L-Arabinose tetraacetate (Wolfrom, et al.: J. Am. Chem. Soc. 63, 201, 1941) was reduced and brominated to give 2,3,4,5-tetra-O-acetylpentyl-1-bromide. This substance (11.8 g) and 5 g of 4-O-alpha-D-glucopyranosylmoranoline were dissolved in 50 ml of dimethylformamide, the solution was added to 6.4 g of anhydrous potassium carbonate, and the mixture was made to react at 100° C. for 5 hours. The reaction solution was filtered and the solvent was evaporated therefrom. The residue was dissolved in water and passed through a column of 100 ml of strongly acidic ion exchange resin [Dowex 50W×2 (H+)]. The column was well washed with water and eluted with 1N ammonia water. The eluate was heated at 70° C. for 1 hour to deacetylate and the solvent was evaporated in vacuo. The residue was dissolved in water and the solution was passed through a column of 100 ml of strongly acidic ion exchange resin [Dowex 50W×2 (H+)]. The column was well washed with water and eluted with 0.5N ammonia water. The solvent was evaporated therefrom. The residue was dried, dissolved in methanol, 4.5 g of p-toluenesulfonic acid monohydrate was added to make it crystallized. After filtration, the crystals were dried and 3.4 g of 4-O-alpha-D-glucopyranosyl-N-(2,3,4,5-tetrahydroxy-n-pentyl)moranoline p-toluenesulfonate was obtained. M.p. 195°–198° C. $[\alpha]_D^{24} = +139.2°$ (c=1%, water).

EXAMPLE 4

4-O-alpha-D-Glucopyranosylmoranoline (5 g) was dissolved in 50 ml of dimethylformamide. To this was added 10 ml of cyclohexene oxide and the mixture was stirred by heating at 110° C. for 20 hours. Then the mixture was diluted with water to wash n-hexane. This was passed through a column of 100 ml of strongly acidic ion exchange resin [Dowex 50W×2 (H+)] to make the object compound adsorbed and washed well with water. The column was eluted with 0.5N ammonia water, the solvent was evaporated therefrom, dried, then dissolved in methanol, and 4.5 g of p-toluenesulfonic acid monohydrate was added to make it crystallized. The mixture was filtered and dried to give 5.8 g of 4-O-alpha-D-glucopyranosyl-N-(2-hydroxycyclohexyl)moranoline. M.p. 105°–108° C. $[\alpha]_D^{24} = +85.0°$ (c=1%, water)

Compounds (IV) can be prepared in the same manner as compounds (I), namely by treating moranoline (II) with an epoxide in an inert solvent, or with a beta-halohydrin in a polar solvent, or with an alpha-haloketone followed by reduction to provide the hydroxy group or groups. See Japanese published patent application No. 54-106,477.

We claim:

1. A compound of the formula I

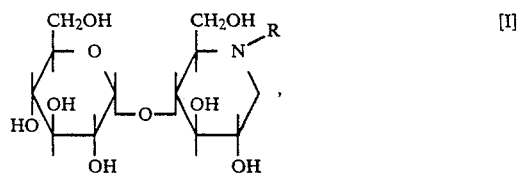

or a pharmaceutically acceptable salt thereof wherein R is alkyl of 1 to 8 carbon atoms substituted by one or more hydroxyl groups.

2. A compound according to claim 1, wherein R is alkyl of 1 to 8 carbon atoms substituted by 1 to 8 hydroxyl groups.

3. A compound according to claim 1, wherein R is alkyl of 1 to 4 carbon atoms substituted by 1 to 4 hydroxyl groups.

4. The compound according to claim 1, which is:
4-O-alpha-D-Glucopyranosyl-N-(2-hydroxyethyl)-moranoline;
4-O-alpha-D-Glucopyranosyl-N-(2-hydroxypropyl)-moranoline;
4-O-alpha-D-Glucopyranosyl-N-(3-hydroxypropyl)-moranolne; or
4-O-alpha-D-Glucopyranosyl-N-(2,3-dihydroxypropyl)moranoline.

5. The compound according to claim 1 which is 4-O-alpha-D-glucopyranosyl-N-(2,3,4,5-tetrahydroxy-n-pentyl)moranoline, the p-toluenesulfonate thereof or 4-O-alpha-D-glucopyranosyl-N-(2-hydroxycyclohexyl)moranoline.

6. A pharmaceutical composition useful for inhibiting an increase in blood sugar level in humans and animals which comprises a therapeutically effective amount of a compound of the formula I

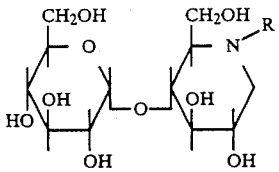

I or a pharmaceutically acceptable salt thereof wherein R is alkyl of 1 to 8 carbon atoms substituted by one or more hydroxyl groups, in combination with a pharmaceutically acceptable carrier.

7. A composition according to claim 6, wherein R is alkyl of 1 to 8 carbon atoms substituted by 1 to 8 hydroxyl groups.

8. A composition according to claim 6, wherein R is alkyl of 1 to 4 carbon atoms substituted by 1 to 4 hydroxyl groups.

9. The composition according to claim 6, wherein the compound is:
4-O-alpha-D-Glucopyranosyl-N-(2-hydroxyethyl)-moranoline;
4-O-alpha-D-Glucopyranosyl-N-(2-hydroxypropyl)-moranoline;
4-O-alpha-D-Glucoporansoyl-N-(3-hydroxypropyl)-moranoline; or
4-O-alpha-D-Glucopyranosyl-N-(2,3-dihydroxypropyl)moranoline.

10. The composition according to claim 6 wherein the compound is 4-O-alpha-D-glucopyranosyl-N-(2,3,4,5-tetrahydroxy-n-pentyl)moranoline, the p-toluenesulfonate thereof or 4-O-alpha-D-glucopyranosyl-N-(2-hydroxycyclohexyl)moranoline.

11. A method for inhibiting an increase in blood sugar level in humans and animals which comprises administering to a human or animal in need thereof a therapeutically effective amount of a compound of the formula I

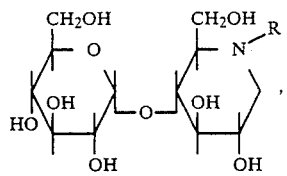

[I]

or a pharmaceutically acceptable salt thereof wherein R is alkyl of 1 to 8 carbon atoms substituted by one or more hydroxyl groups, in combination with a pharmaceutically acceptable carrier.

12. A method according to claim 11, wherein R is alkyl of 1 to 8 carbon atoms substituted by 1 to 8 hydroxyl groups.

13. A method according to claim 11, wherein R is alkyl of 1 to 4 carbon atoms substituted by 1 to 4 hydroxyl groups.

14. The method according to claim 11, wherein the compound is:
4-O-alpha-D-Glucopyranosyl-N-(2-hydroxyethyl)-moranoline;
4-O-alpha-D-Glucopyranosyl-N-(2-hydroxypropyl)-moranoline;
4-O-alpha-D-Glucopyranosyl-N-(3-hydroxypropyl)-moranoline; or
4-O-alpha-D-Glucopyranosyl-N-(2,3-dihydroxypropyl)moranoline.

15. The method according to claim 11 wherein the compound is 4-O-alpha-D-glucopyranosyl-N-(2,3,4,5-tetrahydroxy-n-pentyl)moranoline, the p-toluenesulfonate thereof or 4-O-alpha-D-glucopyranosyl-N-(2-hydroxycyclohexyl)moranoline.

* * * * *